(12) United States Patent
Blacker et al.

(10) Patent No.: US 9,943,958 B2
(45) Date of Patent: Apr. 17, 2018

(54) SYSTEM AND METHOD FOR CONTROLLING A POSITION OF AN ARTICULATED ROBOTIC ARM

(71) Applicant: Corindus, Inc., Waltham, MA (US)

(72) Inventors: Steven J. Blacker, Framingham, MA (US); Stephen Guerrera, Holliston, MA (US); Robert Elden, Cambridge, MA (US)

(73) Assignee: CORINDUS, INC., Waltham, MA (US)

( * ) Notice: Subject to any disclaimer, the term of this patent is extended or adjusted under 35 U.S.C. 154(b) by 227 days.

(21) Appl. No.: 14/732,845

(22) Filed: Jun. 8, 2015

(65) Prior Publication Data

US 2015/0273686 A1   Oct. 1, 2015

Related U.S. Application Data

(63) Continuation-in-part of application No. 14/212,143, filed on Mar. 14, 2014, now Pat. No. 9,070,486.

(60) Provisional application No. 61/791,707, filed on Mar. 15, 2013.

(51) Int. Cl.
| | |
|---|---|
| *G06F 19/00* | (2011.01) |
| *B25J 9/16* | (2006.01) |
| *A61B 6/04* | (2006.01) |
| *A61B 6/00* | (2006.01) |
| *G21F 3/00* | (2006.01) |
| *G21F 7/06* | (2006.01) |

(52) U.S. Cl.
CPC ............ *B25J 9/161* (2013.01); *A61B 6/0407* (2013.01); *A61B 6/461* (2013.01); *A61B 6/547* (2013.01); *B25J 9/1697* (2013.01); *G21F 3/00* (2013.01); *G21F 7/06* (2013.01)

(58) Field of Classification Search
CPC ....... A61B 6/547; A61B 6/461; A61B 6/0407; A61B 6/848; B25J 9/161; B25J 9/1679; B25J 9/1697; B25J 9/0084; B25J 9/41; B25J 9/1648; B25J 9/1641; B25J 9/1689; G21F 3/00; G21F 3/06; G21F 3/08
See application file for complete search history.

(56) References Cited

U.S. PATENT DOCUMENTS

| | | | |
|---|---|---|---|
| 6,726,675 B1 | 4/2004 | Beyar | |
| 7,276,044 B2 * | 10/2007 | Ferry | ................. A61B 1/00147 604/95.01 |
| 7,766,856 B2 * | 8/2010 | Ferry | ................. A61M 25/0113 604/19 |
| 7,887,549 B2 | 2/2011 | Wenderow et al. | |

(Continued)

*Primary Examiner* — Rachid Bendidi
(74) *Attorney, Agent, or Firm* — Rathe Lindenbaum LLP

(57) ABSTRACT

A system for controlling the position of an articulated robotic arm in a robotic catheter procedure system, includes an articulated robotic arm, a first controller coupled to the articulated robotic arm and a patient table. The patient table includes a user interface and a second controller coupled to the user interface and the first controller. The second controller is programmed to generate a control signal in response to a user input received using the patient table user interface, the user input indicating a change in position of the patient table. The second controller is also programmed to transmit the control signal to the patient table and to transmit the control signal to the first controller.

20 Claims, 6 Drawing Sheets

(56) References Cited

U.S. PATENT DOCUMENTS

| | | | | |
|---|---|---|---|---|
| 8,399,871 B2* | 3/2013 | Beyar | ................... | A61B 6/00 |
| | | | | 250/505.1 |
| 2005/0234327 A1* | 10/2005 | Saracen | ............... | A61B 6/0457 |
| | | | | 600/407 |
| 2008/0300458 A1* | 12/2008 | Kim | ................... | A61B 1/00158 |
| | | | | 600/118 |
| 2009/0234444 A1* | 9/2009 | Maschke | ................ | A61B 34/20 |
| | | | | 623/2.11 |
| 2010/0073150 A1* | 3/2010 | Olson | ................... | A61B 34/30 |
| | | | | 340/407.1 |
| 2010/0145358 A1* | 6/2010 | Maschke | ............ | A61B 17/3403 |
| | | | | 606/130 |
| 2011/0238082 A1* | 9/2011 | Wenderow | ........ | A61M 25/0105 |
| | | | | 606/130 |
| 2013/0066135 A1* | 3/2013 | Rosa | ....................... | A61N 5/10 |
| | | | | 600/1 |

* cited by examiner

SYSTEM AND METHOD FOR CONTROLLING A POSITION OF AN ARTICULATED ROBOTIC ARM

CROSS-REFERENCE TO RELATED PATENT APPLICATIONS

This application is a continuation-in-part of U.S. patent application Ser. No. 14/212,143 entitled RADIATION SHIELDING COCKPIT WITH ARTICULATED ROBOTIC ARM filed Mar. 14, 2014, which claims priority to U.S. Provisional Application No. 61/791,707 entitled RADIATION SHIELDING COCKPIT WITH ARTICULATED ROBOTIC ARM filed Mar. 15, 2013, both of which are incorporated herein by reference in their entirety.

BACKGROUND

There are systems for the performance of medical procedures in which a percutaneous device is inserted into a human patient with the guidance of an X-ray image using a mechanism held adjacent to the patient by a robotic arm and the mechanism is controlled from a remote cockpit which provides shielding to the operator of the system from the radiation generated in obtaining the X-ray image. The arm has typically been attached to the patient table by a rail and removed from the rail and placed on the floor or placed in other storage between procedures.

SUMMARY

In accordance with an embodiment, a system for controlling the position of an articulated robotic arm in a robotic catheter procedure system includes an articulated robotic arm, a first controller coupled to the articulated robotic arm and a patient table that includes a user interface and a second controller coupled to the user interface and the first controller, the second controller programmed to generate a control signal in response to a user input received using the patient table user interface, the user input indicating a change in position of the patient table, transmit the control signal to the patient table and transmit the control signal to the first controller In accordance with another embodiment, a system for controlling the position of an articulated robotic arm in a robotic catheter procedure system includes an articulated robotic arm, a first controller coupled to the articulated robotic arm and a visual tracking system that is configured to identify a change in position of a patient table and includes a second controller programmed to generate a control signal in response to identifying a change in position of the patient table, and transmit the control signal to the first controller.

In accordance with another embodiment, a method for controlling a position of an articulated robotic arm in a robotic catheter procedure system includes receiving a user input indicating a change in position of a patient table, generating a control signal in response to the user input, transmitting the control signal to a patient table and to an articulated robotic arm and adjusting a position of the patient table and a position of the articulated robotic arm based on the control signal.

In accordance with another embodiment, a method for controlling a position of an articulated robotic arm in a robotic catheter procedure system includes determining a change in position of a patient table using a visual tracking system, generating a control signal in response to the determination of the change in position of the patient table, transmitting the control signal to a controller coupled to an articulated robotic arm and adjusting a position of the articulated robotic arm based on the control signal.

DETAILED DESCRIPTION

Figure 1A:
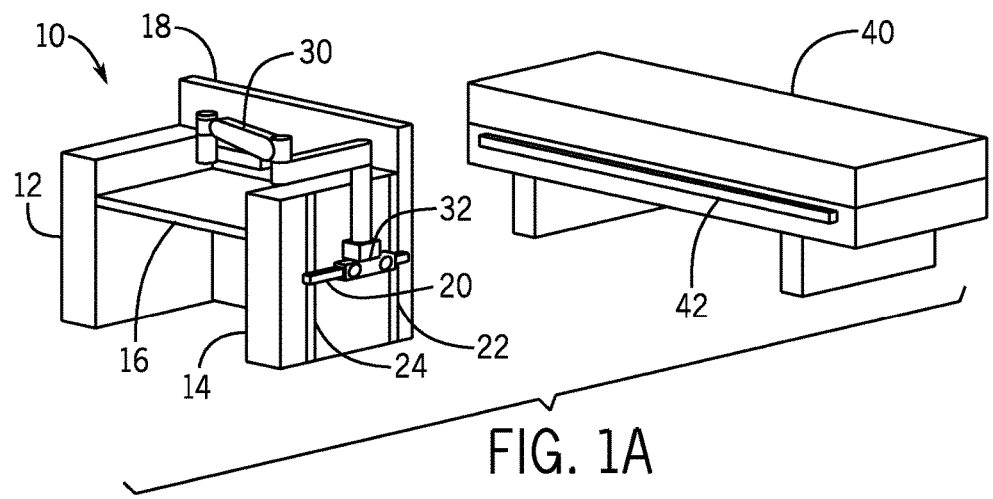
FIG. 1A is a perspective view of a radiation shielding cockpit with an articulated robotic arm attached and an adjacent patient table in accordance with an embodiment.

Referring to FIG. 1A, a radiation shielding cockpit 10 is shown with a left side wall 12, a right side wall 14, a horizontal work table 16 and a front wall 18. Attached to the right side wall 14 is a mounting rail 20. This attachment is via right vertical rail 22 and left vertical rail 24, both of which are attached to the right wall 20. An articulated robotic arm 30 is attached to the mounting rail 20 via an articulated robotic arm mounting bracket 32. The articulated robotic arm 30 is in a stored position with most of its structure lying above the cockpit work table 16. Adjacent the radiation shielding cockpit 10 is a patient table 40 which has an articulated robotic arm mounting bracket 42. In one embodiment to put the system into use and perform a procedure the articulated robotic arm 30 is removed from the mounting rail 20 and attached to the patient table mounting rail 42. After a procedure is completed the articulated robotic arm 30 may be removed from the patient table mounting rail 42 and attached to the cockpit mounting rail 20 thus facilitating its storage out of the way of medical personal who perform their functions such as transport of the patient and preparing the patient table to receive a patient in the close vicinity of the patient table 40.

Figure 1B:
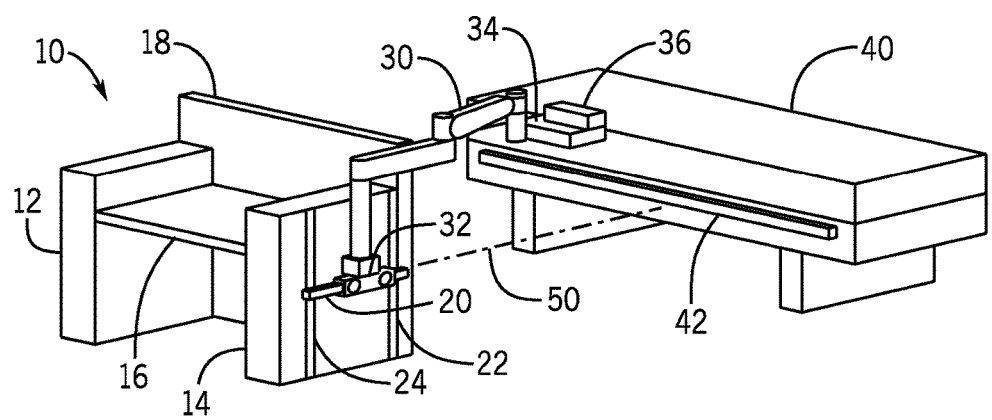
FIG. 1B is a perspective view of a radiation shielding cockpit with an articulated robotic arm attached and deployed above an adjacent patient table in accordance with an embodiment.

Referring to FIG. 1B, a similar arrangement to that of FIG. 1B is shown with the item numbers having the same meaning However, in this case the articulated robotic arm 30 is dynamically mounted to the radiation shielding cockpit 10. The articulated robotic arm 30 includes a mechanism which allows it to track any movements of the patient table 40, particularly in the xy or horizontal plane, and deploy its drive motor mounting base 34 and its attached cassette 36 in a proper orientation to the patient table 40 and therefore the patient (not illustrated). The tracking mechanism of the articulated robotic arm 30 may be instructed by a wireless positioning signal 50. In this embodiment the patient table mounting rail 42 is not used.

Articulated robotic arm 30 may also be controlled in the z direction and automatically adjusted in the vertical z direction by a controller to ensure that the height of the robotic arm 30 is constant with respect to the patient table 40 or patient. This would allow for a constant positioning of a robotic catheter drive with the patient. If the patient moved for example on the table the robotic arm could automatically adjust so that the guide wire or catheter does not move relative to the patient in an undesirable manner.

Although not shown in FIG. 1A or 1B, cockpit 10 may include radiation shields that extend over the walls of the cockpit. In one embodiment, two of the walls have a transparent radiation shield extending upward from the walls, while the third wall remains free of a shield so that the robotic arm may be rotated into the center portion of the cockpit when not in use. Alternatively, a shield may be located on the third wall and removable or may be lowered to allow at least a portion of the robotic arm to swing into the center area of the cockpit when it is desired to store the robotic arm when not in use.

Figure 2:
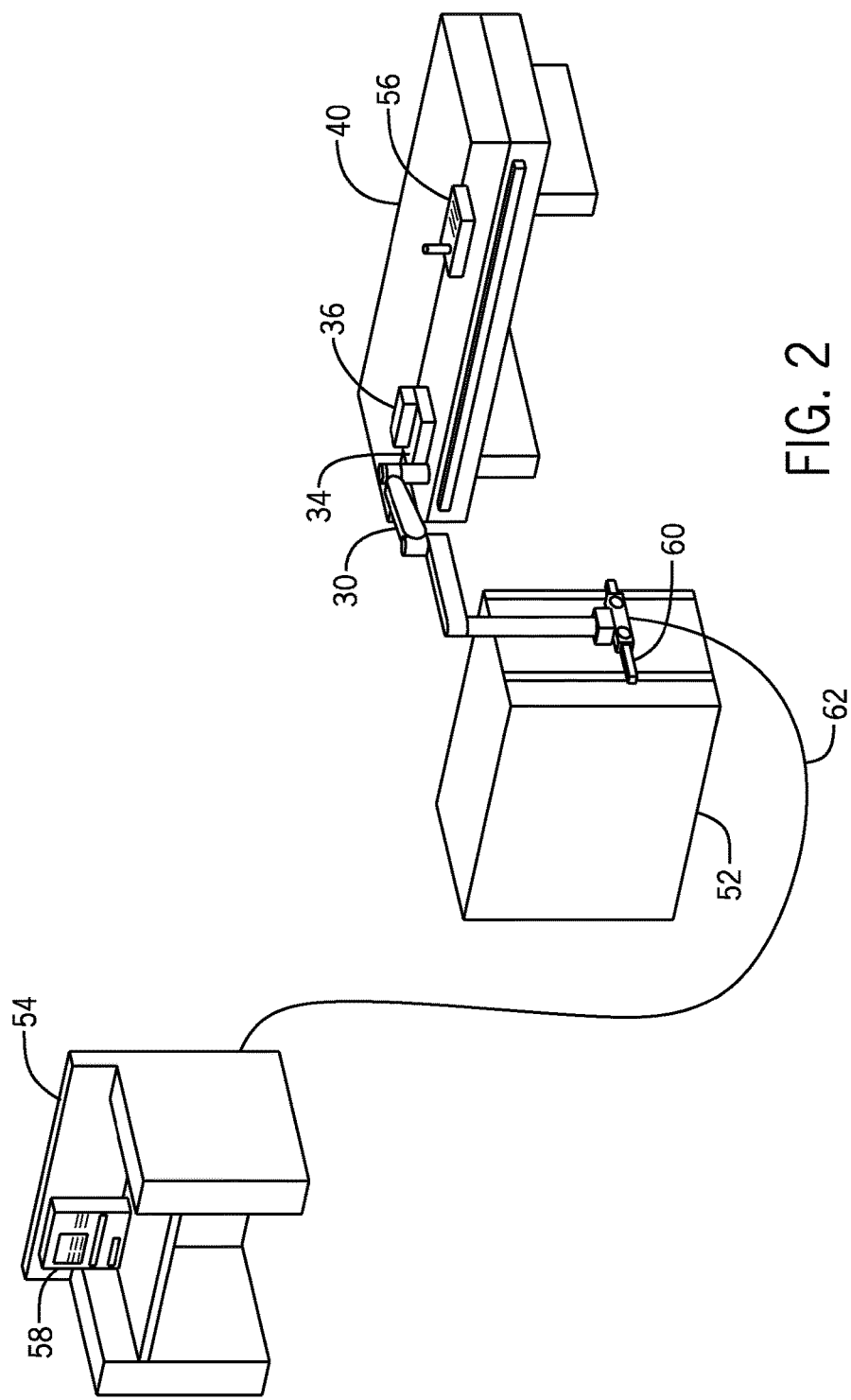
FIG. 2 is a perspective view of a catheter procedure system including a system for controlling a position of an articulated robotic arm in accordance with an embodiment.

In another embodiment, the articulated robotic arm 30 may be mounted to a support that is separate from the radiation shielding cockpit 10 and the patient table 40. FIG. 2 is a perspective view of a catheter procedure system including a system for controlling a position of an articulated robotic arm in accordance with an embodiment. In FIG. 2, an articulated robotic arm 30 is mounted to a support 52 using, for example, a mounting rail 60 on a side of support 52. In other embodiments, the articulated robotic arm 30 may be mounted to support 52 using other known mounting methods. In another embodiment, the articulated robotic arm 30 may be mounted on the top of the support 52. The support 52 may be any structure to which the articulated robotic arm 30 may be mounted such as, for example, a table, a cart with wheels, etc. In one embodiment, support 52 is configured to be moved in a horizontal or vertical direction. For example, the support 52 may include a moveable portion (not shown) and the articulated robotic arm 30 may be mounted to the moveable portion. A drive motor mounting base 34 and cassette 36 are mounted to an end of the articulated robotic arm 30. Cassette 36 is supported by the articulated robotic arm 30 and used to perform a catheter based medical procedure.

A control console or workstation 54 is in communication with the articulated robotic arm 30, support 52, drive motor mounting base 34 and cassette 36 to provide control signals to control the various functions of the articulated robotic arm 30, support 52, drive motor mounting base 34 and cassette 36. Control console 54 may be in communication with articulated robotic arm 30, support 52, drive motor mounting base 34 and cassette 36 via a communication link 62 that may be a wireless connection, cable connection, or any other means capable of allowing communication to occur between the components. Control console 54 includes a user interface 58 configured to receive user inputs to operate various components. User interface 58 includes controls (for example, a touch screen, one or more joysticks, buttons, display monitors, etc.) that allow a user to control the components to perform a catheter based medical procedure. In one embodiment, control console 54 may also be a radiation shielding cockpit and include radiation shields.

The articulated robotic arm 30 and support 52 are positioned adjacent to a patient table 40. Patient table 40 includes a patient table user interface 56 that is used to control the movement and position of the patient table 40. Patient table user interface 56 is configured to receive user inputs and includes controls such as, for example, one or more joysticks, buttons, etc. Patient table user interface 56 may be used to adjust the position of the patient table 40 by causing movement of the patient table 40 in a horizontal direction or a vertical direction.

Control console 54 is also in communication with the patient table 40. In an embodiment, control console 54 and patient table 40 communicate so that the movement of the patient table 40 may be tracked and the position of the articulated robotic arm 30 automatically adjusted to be in the proper orientation with respect to the patient table 40. In another embodiment, the position of support 52 (or a moveable portion of support 52) may be automatically adjusted so that the articulated robotic arm 30 is in the proper orientation with respect to the patient table 40. Control console 54 may be in communication with the patient table 40 via a communication link such as, for example, a wireless connection, cable connection or any other means capable of allowing communication to occur between the components.

Figure 3:
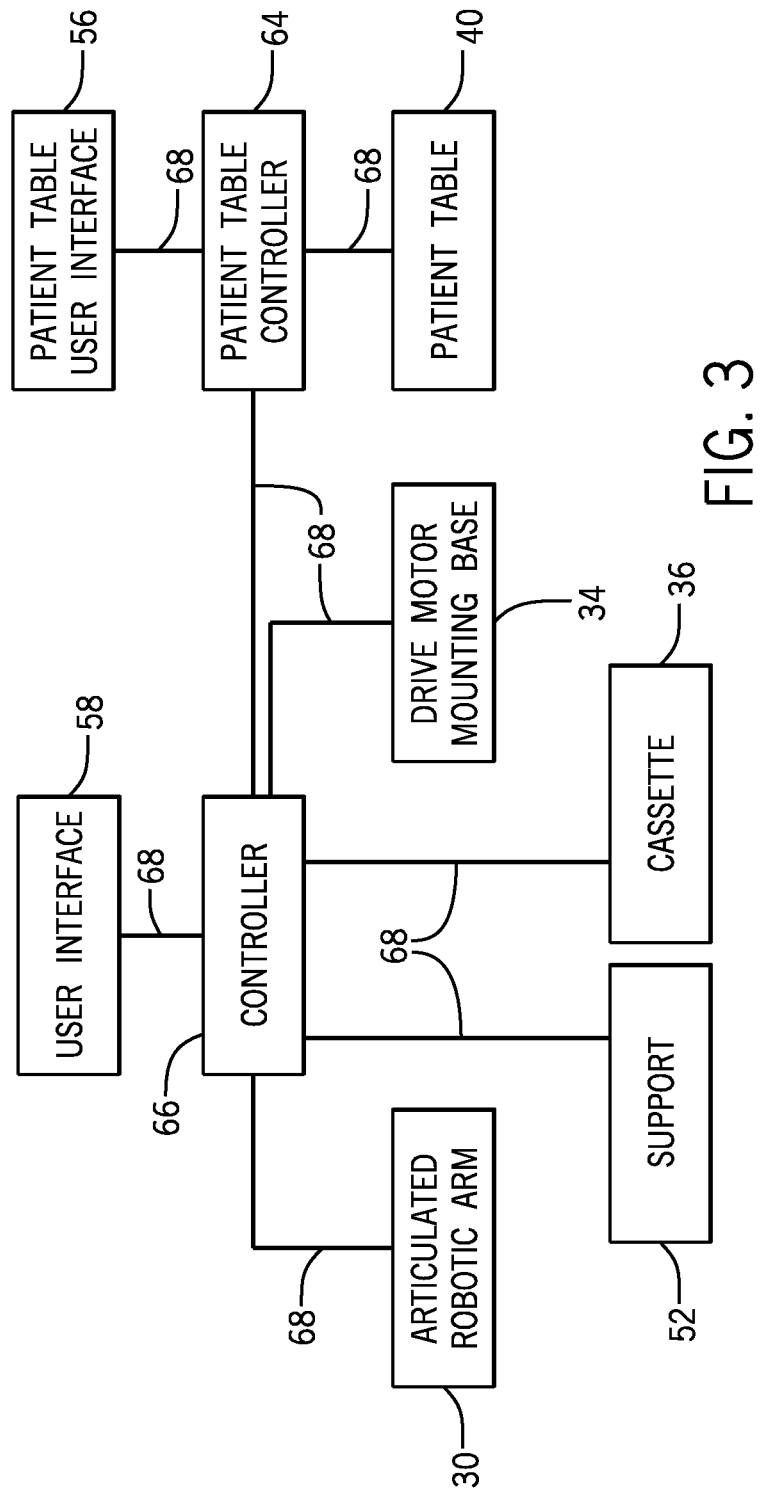
FIG. 3 is a block diagram of a system for controlling a position of an articulated robotic arm in a catheter procedure system in accordance with an embodiment.

FIG. 3 is a block diagram of a system for controlling a position of an articulated robotic arm in a catheter procedure system in accordance with an embodiment. Control console 54 (shown in FIG. 2) includes a controller (or first controller) 66 and patient table 40 (shown in FIG. 2) includes a patient table controller (or second controller) 64. Controller 66 and patient table controller 64 may be electronic control units suitable to provide the various functionalities described herein. Controller 66 is in communication with user interface 58, articulated robotic arm 30, support 52, drive motor mounting base 34 and cassette 36 via for example, communication links 68. In one embodiment, controller 66 may be located within control console 54 or in other embodiments, controller 66 may be located remotely from control console 54. Patient table controller 64 is in communication with patient table user interface 56 and patient table 40 via, for example, communication links 68.

Patient table controller 64 is also in communication with controller 66 via a communication link 68. Communication links 68 may be wired or wireless connections. Communication links 68 may also represent communication over a network. Patient table controller 64 is configured to generate control signals in response to a user's interaction with patient table user interface 56. In one embodiment, patient table controller 64 generates control signals to control the movement and position of the patient table 40 based on user input. The patient table controller 64 is also configured to transmit the control signals indicating the movement of the patient table 40 to the controller 66. In one embodiment, controller 66 may then automatically adjust the position of the articulated robotic arm 30 based on the control signal received from the patient table controller 64 so the articulated robotic arm 30 is in the proper orientation with respect to the patient table 40. As discussed above with respect to FIG. 2, the position of the patient table 40 and articulated robotic arm 30 may be adjusted in horizontal, vertical and transverse directions. In another embodiment, controller 66 may then automatically adjust the position of the support 52 (or a moveable portion of support 52) based on the control signal received from the patient table controller 64 so the articulated robotic arm 30 is in the proper orientation with respect to the patient table 40. The position of the support 52 may be adjusted in both the horizontal and vertical directions.

Figure 4:
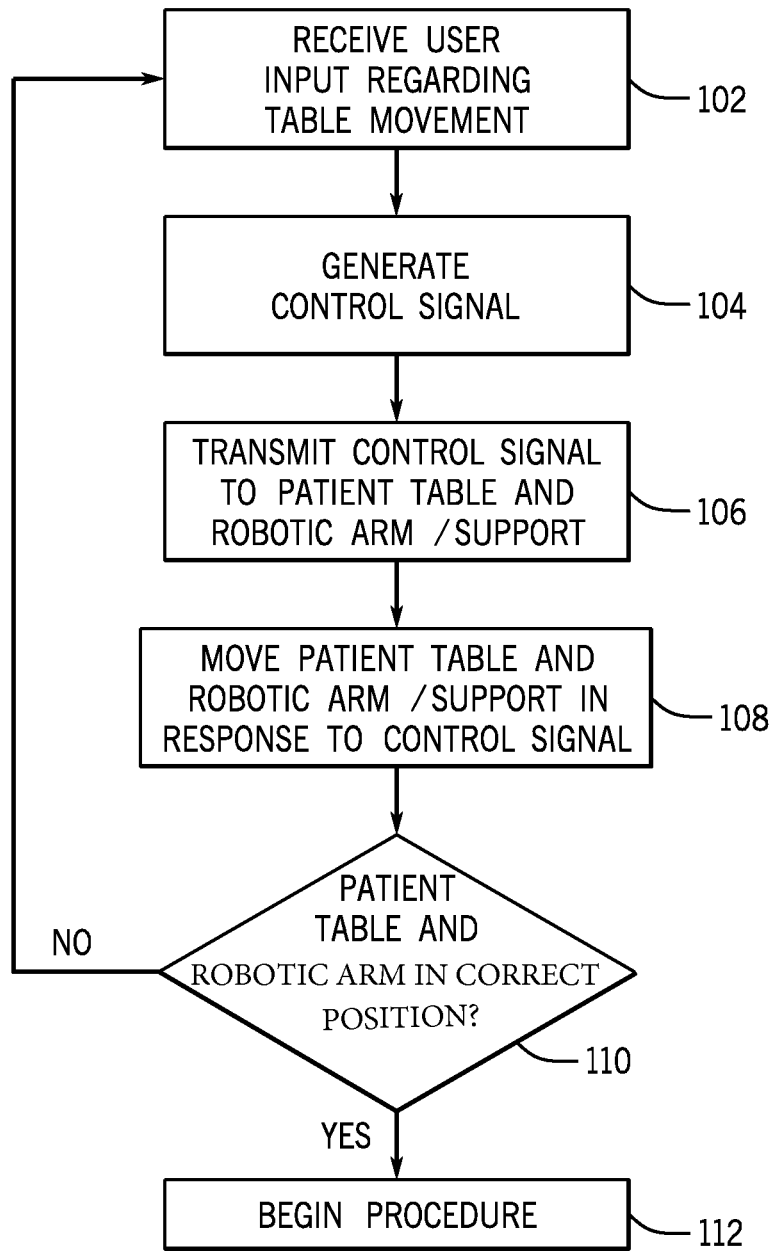
FIG. 4 illustrates a method for controlling a position of an articulated robotic arm in a catheter procedure system in accordance with an embodiment.

FIG. 4 illustrates a method for controlling a position of an articulated robotic arm in a catheter procedure system in accordance with an embodiment. At block 102, a user input is received via, for example, patient table user interface 56, indicating movement of the patient table 40. A control signal is generated at block 104 by, for example, patient table controller 64 and transmitted to the patient table and to either the articulated robotic arm or the support. At block 108, the patient table and either the articulated robotic arm or the support are automatically moved in response to the control signal. If the patient table and articulated robotic arm are in the correct position at block 110, the user may proceed with the catheter based medical procedure at block 112. If the patient table and articulated robotic arm are not in the correct position at block 110, the process returns to block 102 and additional user inputs may be received to further adjust the position of the patient table and articulated robotic arm.

Figure 5:
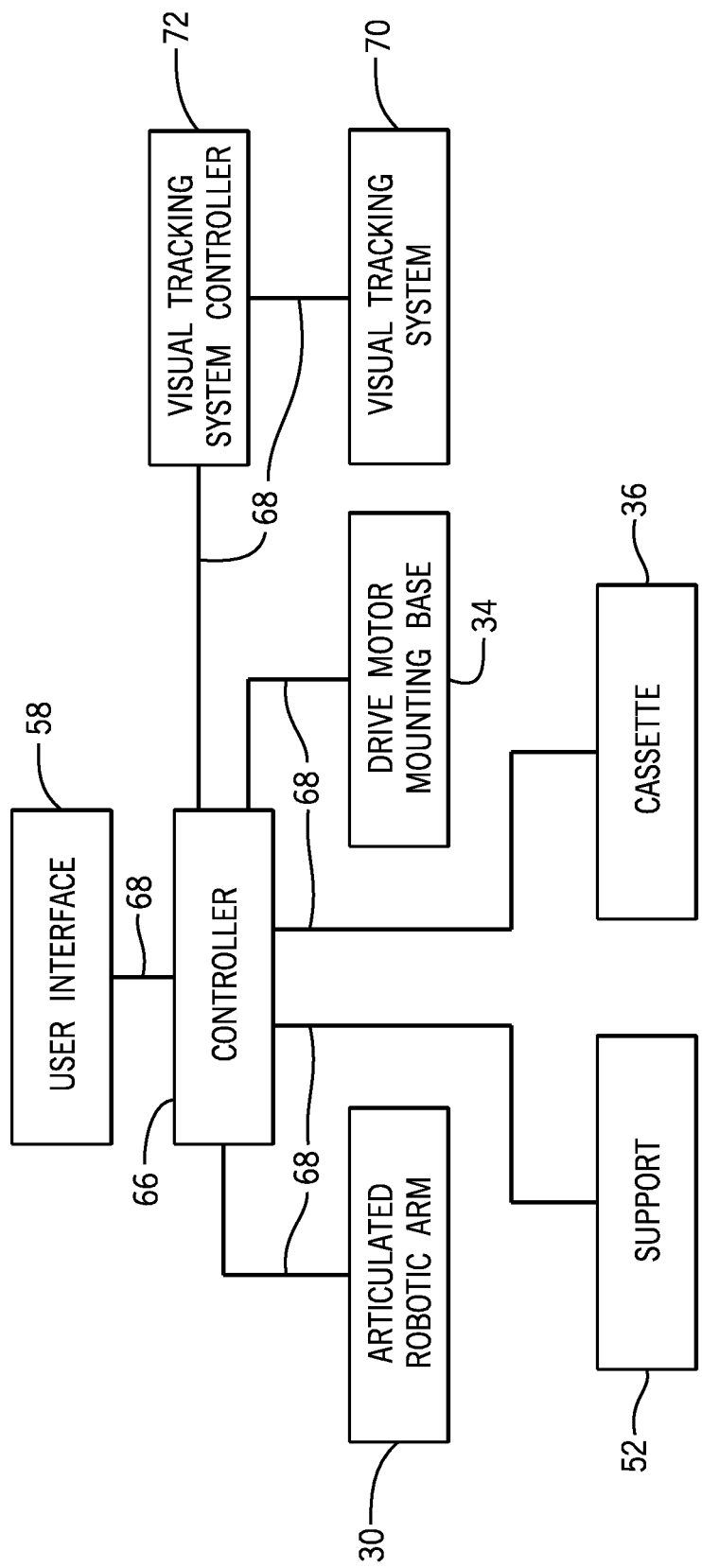
FIG. 5 is a block diagram of a system for controlling a position of an articulated robotic arm including a visual tracking system in accordance with an embodiment.

In another embodiment, a visual tracking system may be used to track the movement of the patient table and provide a control signal to automatically adjust the position of the support or the articulated robotic arm so that the articulated robotic arm is in the proper orientation with respect to the patient table. FIG. 5 is a block diagram of a system for controlling a position of an articulated robotic arm including a visual tracking system in accordance with an embodiment. A control console (such as control console 54 shown in FIG. 2) includes a controller 66. A visual tracking system 70 includes a visual tracing system controller 72. Visual tracking system 70 may be any device capable of visually tracking the movement of the patient table 40 (shown in FIG. 2) such as one or more video cameras. The one or more video cameras may be positioned in proximity to the patient table. Video signals may be provided from, for example, the cameras to the visual tracking system controller 72 and the controller 72 may generate a control signal to indicate the movement of the patient table.

The visual tracking system controller 72 is in communication with controller 66 via a communication link 68. Communication links 68 may be wired or wireless connections. Communication links 68 may also represent communication over a network. The visual tracking system controller 72 is configured to transmit the control signal indicating the movement of the patient table to the controller 66. In one embodiment, controller 66 may then automatically adjust the position of the articulated robotic arm 30 based on the control signal received from the visual tracking system controller 64 so the articulated robotic arm 30 is in the proper orientation with respect to the patient table 40. As discussed above, the position of the patient table 40 and articulated robotic arm 30 may be adjusted in horizontal, vertical and transverse directions. In another embodiment, controller 66 may then automatically adjust the position of the support 52 (or a moveable portion of support 52) based on the control signal received from the patient table controller 64 so the articulated robotic arm 30 is in the proper orientation with respect to the patient table 40. The position of the support 52 may be adjusted in both the horizontal and vertical directions.

Figure 6:
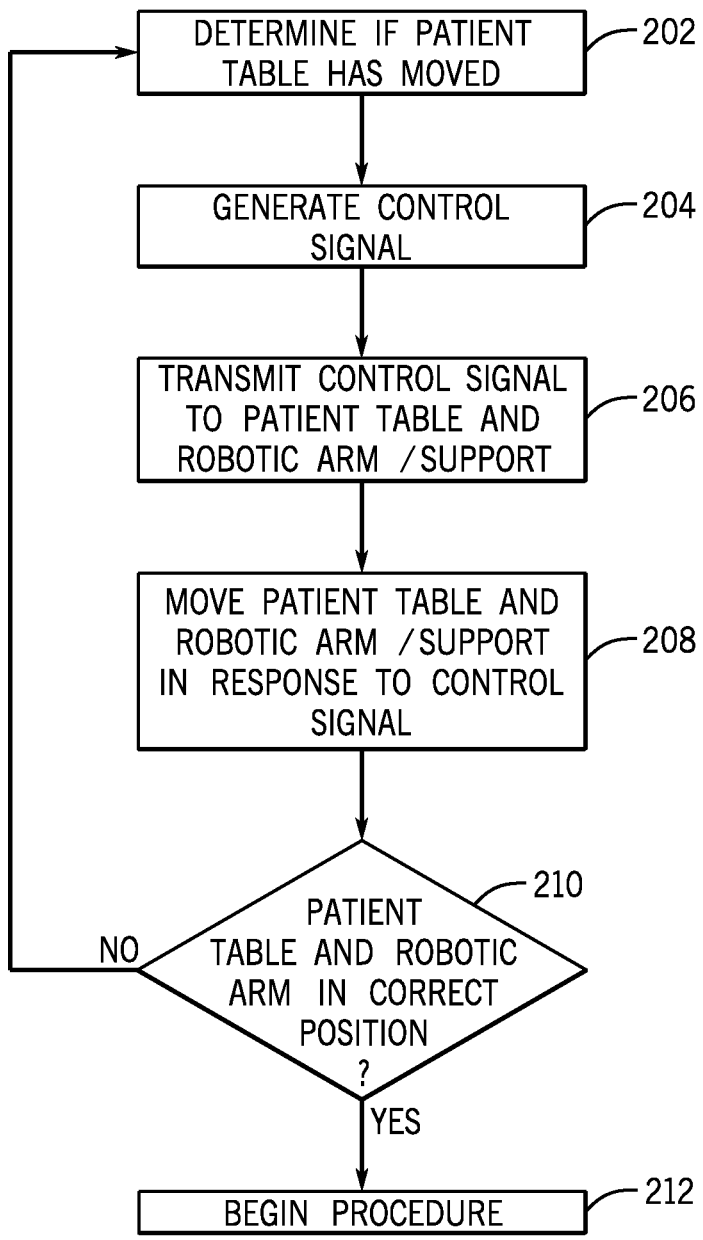
FIG. 6 illustrates a method for controlling a position of an articulated robotic arm in a catheter procedure system in accordance with an embodiment.

FIG. 6 illustrates a method for controlling a position of an articulated robotic arm in a catheter procedure system in accordance with an embodiment. At block 202, it is determined if the patient table has been moved, for example, using a visual tracking system 70. In one embodiment, the visual tracking system may include one or more cameras positioned in proximity to the patient table. A control signal is generated at block 204 by, for example, visual tracking system controller 72 and transmitted to the patient table and to either the articulated robotic arm or the support. At block 208, the patient table and either the articulated robotic arm or the support are automatically moved in response to the control signal. If the patient table and articulated robotic arm are in the correct position at block 210, the user may proceed with the catheter based medical procedure at block 212. If the patient table and articulated robotic arm are not in the correct position at block 210, the process returns to block 202.

While only certain features of the invention have been illustrated and described herein, many modifications and changes will occur to those skilled in the art. It is, therefore, to be understood that the appended claims are intended to cover all such modifications and changes as fall within the true spirit of the invention. A number of features are disclosed herein. These features may combined in multiple combinations such that features may be used alone or in any combination with any of the other features.

What is claimed is:

1. A system for controlling the position of an articulated robotic arm, the system comprising:
   a robotic catheter procedure system comprising:
      the articulated robotic arm; and
      a first controller coupled to the articulated robotic arm; and
   a patient table positioned proximate to and separate from the articulated robotic arm, the patient table comprising:
      a patient table user interface configured to control movement of the patient table; and
      a patient table controller coupled to the patient table user interface and the first controller, the patient table controller programmed to:
         generate a control signal in response to a user input received using the patient table user interface, the user input indicating a change in position of the patient table;
         transmit the control signal to the patient table to adjust the position of the patient table based on the user input indicating the change in position of the patient table; and
         in response to the user input indicating the change in position of the patient table, transmit the control signal to the first controller to adjust the position of the articulated robotic arm based on the change in position of the patient table.

2. The system according to claim 1, wherein the articulated robotic arm is mounted on a support.

3. The system according to claim 2, wherein the first controller adjusts the position of the support in response to the control signal.

4. The system according to claim 1, further comprising a drive motor mounting base and a cassette attached to the articulated robotic arm.

5. The system according to claim 1, wherein the change in position of the patient table is in a horizontal direction and the first controller adjusts the position of the articulated robotic arm in a horizontal direction in response to the control signal.

6. The system according to claim 1, wherein the change in position of the patient table is in a vertical direction and the first controller adjusts the position of the articulated robotic arm in a vertical direction in response to the control signal.

7. The system according to claim 1, wherein the first controller adjusts a position of the articulated robotic arm in a transverse direction in response to the control signal.

8. A system for controlling the position of an articulated robotic arm, the system comprising:
   a robotic catheter procedure system comprising:
      the articulated robotic arm; and
      a first controller coupled to the articulated robotic arm;

a patient table positioned proximate to and separate from the articulated robotic arm, the patient table; and a visual tracking system configured to identify a change in the position of the patient table and comprising a second controller programmed to:

generate a control signal in response to identifying the change in position of the patient table; and in response to the change in position of the patient table, transmit the control signal to the first controller to adjust the position of the articulated robotic arm based on the change in position of the patient table.

9. The system according to claim 8, wherein the articulated robotic arm is mounted on a support.

10. The system according to claim 9, wherein the first controller adjusts the position of the support in response to the control signal.

11. The system according to claim 8, wherein the first controller adjusts the position of the articulated robotic arm in response to the control signal.

12. The system according to claim 8, wherein the visual tracking system comprises at least one video camera.

13. A method for controlling a position of an articulated robotic arm in a robotic catheter procedure system, the articulated robotic arm coupled to a first controller which is in communication with a patient table controller of a patient table, the patient table controller coupled to a patient table user interface, the method comprising:

receiving a user input indicating a change in position of the patient table;

generating a control signal using the patient table controller in response to the user input;

transmitting the control signal to the patient table, the patient table positioned proximate to and separate from the articulated robotic arm;

adjusting the position of the patient table based on the control signal;

in response to the user input indicating the change in position of the patient table, transmitting the control signal from the patient table controller to the articulated robotic arm; and adjusting the position of the articulated robotic arm based on the control signal.

14. The method according to claim 13, wherein the change in position of the patient table is in a horizontal direction and the position of the patient table and the articulated robotic arm are adjusted in a horizontal direction in response to the control signal.

15. The method according to claim 13, wherein the change in position of the patient table is in a vertical direction and the position of the patient table and the articulated robotic arm are adjusted in a vertical direction in response to the control signal.

16. The method according to claim 13, wherein the position of the articulated robotic arm is adjusted in a transverse direction in response to the control signal.

17. The method according to claim 13, wherein the position of the articulated robotic arm is adjusted by changing a position of a support on which the articulated robotic arm is mounted.

18. A method for controlling a position of an articulated robotic arm in a robotic catheter procedure system, the articulated robotic arm coupled to a first controller which is in communication with a visual tracking system having a second controller, the method comprising:

determining a change in position of a patient table using the visual tracking system, the patient table positioned proximate to and separate from the articulated robotic arm;

generating a control signal using the second controller in response to the determination of the change in position of the patient table;

in response to the change in position of the patient table, transmitting the control signal from the second controller to the first controller coupled to the articulated robotic arm; and adjusting a position of the articulated robotic arm based on the control signal.

19. The method according to claim 18, wherein the position of the articulated robotic arm is adjusted by changing the position of a support on which the articulated robotic arm is mounted.

20. The method according to claim 19, wherein the change of position of the patient table is determined using at least one video camera.

* * * * *